United States Patent [19]

Cole et al.

[11] Patent Number: 4,601,712
[45] Date of Patent: Jul. 22, 1986

[54] DRIP CHAMBER

[75] Inventors: James E. Cole, Ventura; Norman H. Sears, Westlake Village, both of Calif.

[73] Assignee: Gould Inc., Rolling Meadows, Ill.

[21] Appl. No.: 552,562

[22] Filed: Nov. 16, 1983

[51] Int. Cl.$^4$ .............................................. A61M 5/16
[52] U.S. Cl. ..................................... 604/251; 604/122
[58] Field of Search ................. 604/49, 140, 145, 148, 604/246, 122, 251-253

[56] References Cited

U.S. PATENT DOCUMENTS

| | | | |
|---|---|---|---|
| 2,335,799 | 11/1943 | Schwab | 604/148 |
| 2,725,056 | 11/1955 | Tash | 604/148 |
| 2,989,052 | 6/1961 | Broman | 128/214 |
| 3,004,590 | 10/1961 | Rosenblad | 159/13 |
| 3,030,954 | 4/1962 | Thornton | 604/251 |
| 3,584,770 | 6/1971 | Taylor | 604/141 X |
| 3,881,640 | 5/1975 | Noble | 604/246 X |

FOREIGN PATENT DOCUMENTS

| | | |
|---|---|---|
| OLS2226891 | 12/1972 | Fed. Rep. of Germany . |
| 154629 | 5/1956 | Sweden .............................. 604/251 |
| 2077414A | 12/1981 | United Kingdom . |

Primary Examiner—Dalton L. Truluck
Attorney, Agent, or Firm—Robert J. Fox; G. Paul Edgell; Edward E. Sachs

[57] ABSTRACT

An improved conduit (50) communicating between a pressurized source (10) of solution and a partially filled reservoir (34) associated with a drip chamber (24) in a continuous-flush system. The conduit comprises a tube (54,56) that is bent at approximately a 45 degree angle so that solution discharging from the conduit (50) is diverted to impinge against the interior wall (58) of the reservoir (34) before interfacing with the solution (62) accumulated therein. The arrangement reduces bubble formation normally associated with turbulent discharge flow during filling and flushing of the system.

1 Claim, 4 Drawing Figures

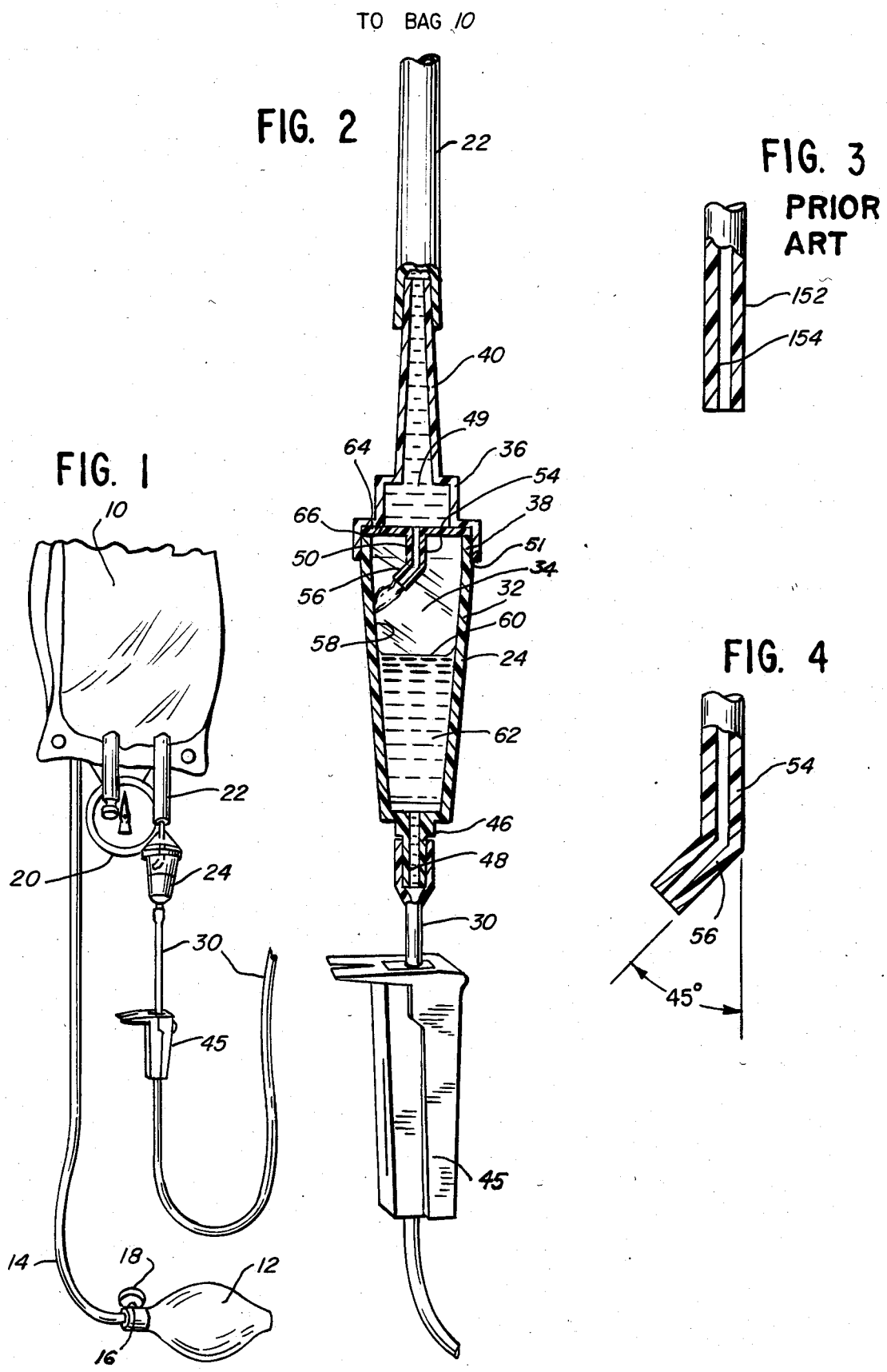

DRIP CHAMBER

BACKGROUND OF THE INVENTION

1. Field of the Invention

This invention relates to systems for infusion monitoring and, more particularly, to an apparatus and method for preventing bubble formation in a drip chamber during filling or fast flushing.

2. Background Art

Hemodynamic monitoring of surgical and other seriously ill patients is a commonly accepted practice, vital to the medical management of the patient. In order to sense the desired pressure for registration or recording, a blood vessel in the patient must be cannulated. That is, a conduit filled with relatively incompressible liquids must be established from the pressure site within the patient out to an appropriate instrumentation system.

Although the conduit, or pressure-monitoring line, may be filled in its entirety with a liquid, such as sterile, isotonic saline solution containing a diluted anticoagulant agent, the tip of the cannula must interface with the patient's blood. Due to diffusion, and in arterial pressure procedures, affected by pulsations, the blood may coagulate, forming a clot that is hazardous to the patient and introducing serious errors in the pressure measurement. The coagulation process is aggravated by even the slightest leak in the liquid-filled system.

Since the cannula must often remain in place for an extended period in an unimpaired, clot-free condition, considerable effort has been expended to achieve this goal. A known solution is to incorporate a capillary tube connected to a pressurized source of liquid, allowing a slow, continuous flow through the cannula into the patient. A volume of two to four cubic centimeters (cc) per hour has been found effective in the case of an adult, without interfering with the ongoing pressure monitoring.

One variation of the system described above affords an optional rapid-flow mode from the pressurized solution source for initial filling and debubbling of the system and later flushing of the line after a blood sample has been taken. Typical systems in common use incorporate a drip chamber located near the pressurized liquid source, in series with the administration set line. The drip chamber has proved to be a primary source of air bubble formation.

This chamber is kept only partially full, so that liquid entering it forms drops from a tube, thereby establishing a visible indication of flow volume. Due to potential differences in the flow devices mentioned in the preceding paragraph, the rate may deviate from the specified range of two to four cc per hour. It is common practice to size the input tube so that each drop per minute into the chamber represents a flow volume of one cc per hour. By observation of the drip chamber for one minute, the flow rate can be determined.

Development of this desirable flow indicator has resulted in the use of a very small diameter drip tube. When the fast-flush mode of the flow device is actuated, the small diameter causes the liquid to form a high-speed jet. A Venturi effect results, causing air to entrain in the fluid stream, which creates great turbulence and aeration in the chamber and frothing of the liquid. A train of air bubbles will be drawn into the administration line and then into the flow device and on into the patient. Such bubbles are a life-threatening hazard to the patient and produce intolerable distortion in the pressure measurements.

One proposed solution to the problem of bubble formation is the installation of a filter at the lower region of the drip chamber. While the filter tends to intercept and screen out larger bubbles, microscopic bubbles will penetrate even very fine filtering at high flow rates and under severely turbulent conditions. This phenomenon may be observed when the otherwise clear, transparent solution appears somewhat gray in color as it passes through the filter. Later, colescence of these fine bubbles downstream in the administration line results in visible bubbles that constitute a hazard.

The present invention is directed to overcoming one or more of the problems enumerated above.

SUMMARY OF THE INVENTION

The present invention is an improvement in a drip chamber associated with a continuous-flush system for infusion-monitoring of patients. The basic system with which the invention is particularly adaptable consists of a source of pressurized solution and an administration line which delivers the solution between the source and an intravenous device through which the solution is administered to the patient. The drip chamber is provided in the administration line to determine the rate of infusion and is filled partially with the solution to a liquid level.

According to the invention, a conduit is provided to control the introduction of solution into a reservoir in the drip chamber during filling and/or flushing, during which the tendency to create air bubbles is exaggerated. The conduit is configured to discharge the solution into the reservoir and cause the solution to impinge on the interior wall surface of the reservoir in nonparallel relationship with such surface above the liquid level before interfacing with the solution in the reservoir at the liquid level.

In one form the conduit comprises a rigid tube with a first portion having an integral mounting element. The mounting element is captured in assembled situation by a cap mating with a housing defining the reservoir. The tube is bent, preferably at a 45 degree angle from the first portion to define a discharge portion which appropriately diverts the solution introduced to the drip chamber.

Other objects and advantages of the invention will be apparent from the following detailed description, the drawing, and the appended claims.

BRIEF DESCRIPTION OF THE DRAWING

FIG. 1 is an elevational view of a conventional continuous-flush system having a drip chamber which incorporates the arrangement of the invention.

FIG. 2 is a sectional view of a drip chamber incorporating the arrangement of the invention.

FIG. 3 is an enlarged, fragmentary view of the discharge end of a prior art conduit for admitting solution to a drip chamber.

FIG. 4 is an enlarged, fragmentary view of the discharge end of a conduit according to the present invention.

DETAILED DESCRIPTION OF THE DRAWING

A conventional continuous-flush system, with which the present invention is operable, is illustrated in FIG. 1. A flexible pressure bag 10 retains a supply of solution, which is typically saline, in an elevated position. A preselected pressure is developed in the bag 10 by a hand-operated bulb 12 which communicates with the bag 10 through a flexible tube 14. A valve 16 with a thumb-operated control 18 permits pressure relief in the bag 10. A conventional manometer 20 is provided to measure the pressure in bag 10.

An outlet 22 is provided at the bottom of bag 10 to discharge solution into a drip chamber 24, which is partially filled with the saline solution. The drip chamber 24 is transparent so that the rate of administration of the solution to the patient can be determined by observing the drip rate into chamber 24 and the height of the liquid level 26. An outlet 28 with a reduced cross section connects an administration tube 30 with the chamber. Tube 30 extends to a point of infusion, which is accomplished in conventional manner and does not form part of the present invention.

The details of drip chamber 24 and the invention, which is associated directly therewith, are shown in FIGS. 2 and 4, with conventional structure over which the instant invention is an impovement shown in FIG. 3.

Drip chamber 24 comprises a main transparent housing 32 which is configured substantially as a truncated cone and defines a solution-accumulating reservoir 34. A durable, high-quality plastic is preferably used to construct housing 32. A stepped cap 36 is surroundingly fit over the upper free edge 38 of housing 32 and has an integral spike 40 which inserts into and mates closely in fluid-tight engagement with outlet 22 of bag 10.

The bottom of housing 32 has reduced male end fitting 46 defining an outlet passage 48. An expanded end of administration tube 30 mates closely with fitting 46 in conventional manner. A line clamp 45 is provided to manually arrest the flow of solution in tube 30.

A chamber 49, defined by stepped cap 36, communicates with reservoir 34 of the drip chamber 24 through an intermediate conduit 50 which embodies the instant invention. The conduit 50 comprises a first, vertically extending portion 54 and is bent to define a discharge portion 56. According to the invention, conduit 50 routes the solution so that it impinges in nonparallel relationship against the interior wall surface 58 of reservoir 34 above liquid level 60 and before interfacing with solution 62 at the bottom of drip chamber 24. This arrangement reduces bubble formation in chamber 24. To further preclude the passage of bubbles through the system, a fine bubble filter (not shown) may be inserted at the bottom of the drip chamber, as is well known.

To assemble conduit 50 with drip chamber 24, an integral, concentric, disc-shaped mounting body 64 is provided which is integral with the conduit 50. Mounting body 64 is captured between the upper edge 38 of housing 32 and a shoulder 66 defined by stepped cap 36 with the cap 36 and housing 32 in assembled relationship. The body seats closely in cylindrical end 51 of the cap 36 and 64 thereby consistently locates conduit 50 in concentric relation with the housing 32 during assembly.

Conduit 50 preferably is bent at a 45 degree angle so that the solution impinges at approximately the same angle against interior wall surface 58. The conduit preferably is fabricated from noncorrosive metal. However, it may be made from plastic or other substantially rigid material of suitable durability.

A prior art conduit 152 is illustrated in FIG. 3 and comprises a cylindrical tube with a straight central passageway 154. The majority of solution from the bag interfaces with solution in the chamber before contacting the interior wall surface of the chamber. In this chamber, the problem of bubble formation is prevalent.

The method of the invention will be apparent from the foregoing description of the apparatus thereof.

The foregoing description is given for clearness of understanding only, and no unnecessary limitations should be implied therefrom, as modifications will be obvious to those skilled in the art.

We claim:

1. A non-aerating drip chamber for use with a pressurized source of intravenous solution for precisely metering a rate of flow of intravenous solution at a low flow rate and for preventing aeration of intravenous solution at a high rate of flow of said intravenous solution, comprising: a truncated cone top cap having a first end connected in frictional engagement with an intravenous delivery line and having a second end comprising a snap collar; an intermediate member having a partition with a drip tube connected thereto, the drip tube extending downwardly from the partition and having a first section oriented substantially perpendicular to the partition and connected thereto and a second angled section connected to the first section, the partition abutting a shoulder of the top cap; and a lower truncated cone reservoir having a first end abutting the partition opposite the top cap and frictionally engaged by the snap collar of the top cap to define a closed volume whereby the second angled section of the drip tube extends downwardly into the lower truncated cone reservoir and is positioned in proximity with a sidewall of the lower truncated cone reservoir, the lower truncated cone reservoir having a tube connected thereto for carrying intravenous fluid delivered through the top cap and the drip tube out of the bottom of the drip chamber.

* * * * *